(12) United States Patent
Anders

(10) Patent No.: US 8,750,995 B2
(45) Date of Patent: Jun. 10, 2014

(54) HEART MONITORING DEVICE

(75) Inventor: Björling Anders, Järfalla (SE)

(73) Assignee: St. Jude Medical AB, Jarfalla (SE)

(*) Notice: Subject to any disclaimer, the term of this patent is extended or adjusted under 35 U.S.C. 154(b) by 1432 days.

(21) Appl. No.: 11/916,596

(22) PCT Filed: Jun. 16, 2005

(86) PCT No.: PCT/SE2005/000943
§ 371 (c)(1),
(2), (4) Date: Dec. 5, 2007

(87) PCT Pub. No.: WO2006/135291
PCT Pub. Date: Dec. 21, 2006

(65) Prior Publication Data
US 2008/0194974 A1    Aug. 14, 2008

(51) Int. Cl.
*A61B 5/04* (2006.01)
*A61N 1/00* (2006.01)

(52) U.S. Cl.
USPC ............ 607/17; 600/508; 600/509; 600/510; 600/513; 600/515; 600/516; 600/517; 607/9; 607/25; 607/27; 607/28; 607/30

(58) Field of Classification Search
USPC ............ 607/9, 25, 27, 28, 30; 600/508, 509, 600/510, 513, 515, 516, 517
See application file for complete search history.

(56) References Cited

U.S. PATENT DOCUMENTS

| | | | |
|---|---|---|---|
| 5,560,368 A * | 10/1996 | Berger | 600/517 |
| 5,800,471 A | 9/1998 | Baumann | |
| 6,424,865 B1 | 7/2002 | Ding | |
| 6,643,548 B1 * | 11/2003 | Mai et al. | 607/17 |
| 6,748,261 B1 | 6/2004 | Kroll et al. | |
| 6,763,267 B2 | 7/2004 | Ding | |
| 2002/0062139 A1 * | 5/2002 | Ding | 607/25 |

* cited by examiner

Primary Examiner — Niketa Patel
Assistant Examiner — Lindsey G Hankins

(57) ABSTRACT

An implantable heart stimulating device for indicating congestive heart failure (CHF) has a processor and a sensor combination that senses at least two heart events during one heart cycle at different locations of the heart. The processor is supplied with signals from the sensor combination relating to the sensed events, and determines therefrom at least one heart time interval between the sensed events in the same heart cycle. The processor determines a CHF indicator value representing a degree of CHF based on a variability measure calculated from at least two heart time intervals from at least two different heart cycles. The processor determines the CHF indicator value in relation to previous CHF indicator values.

14 Claims, 2 Drawing Sheets

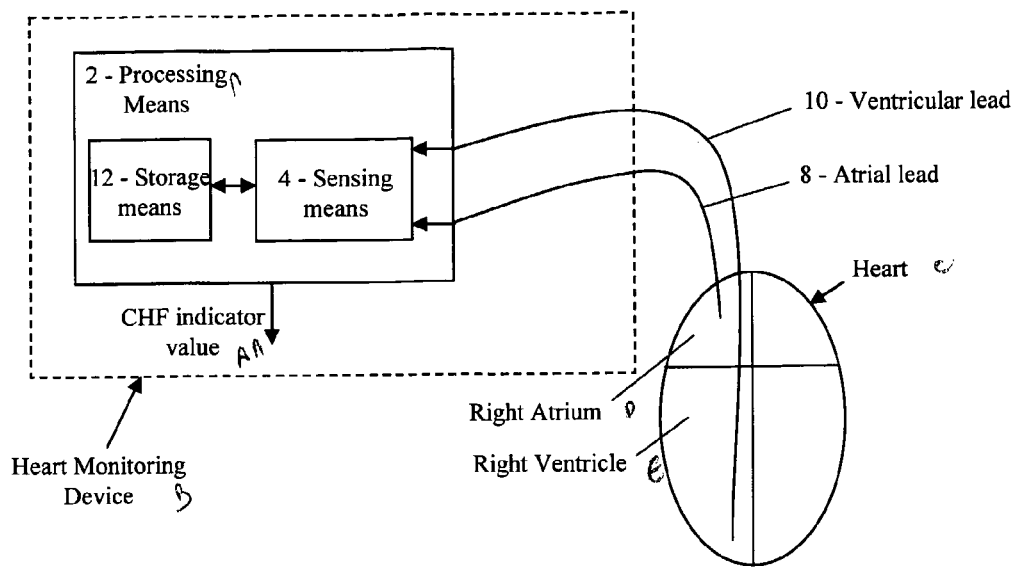
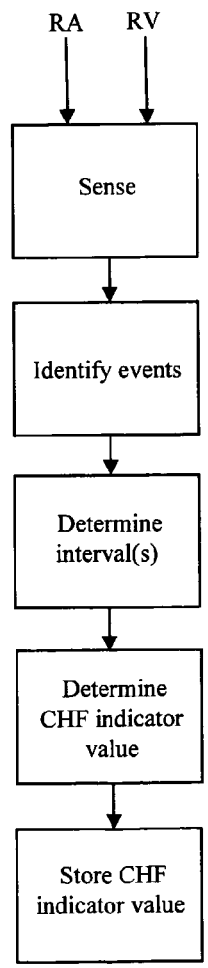
Fig. 1
Fig. 2

HEART MONITORING DEVICE

BACKGROUND OF THE INVENTION

1. Field of the Invention

The present invention relates to a heart monitoring device to measure and quantify the degree of congestive heart failure. A determined congestive heart failure indicator value—alone or together with other metrics—may advantageously be used in assessing the patient's status, titrating drugs and/or evaluating therapy.

The invention may be applied to all dual chamber devices, preferably biventricular devices, implanted for the treatment of CHF. No specialized leads or hardware is required. The invention is also applicable by using a conventional ECG equipment provided with surface electrodes.

2. Description of the Prior Art

Approximately 23 million people worldwide are afflicted with congestive heart failure (CHF), and 2 million new cases of CHF are diagnosed each year worldwide. In contrast to other cardiovascular disorders that have actually declined during the past few decades, the incidence of heart failure is one that rises. It is, in fact, the most rapidly growing cardiovascular disorder in the United States.

Congestive heart failure is a chronic inability of the heart to maintain an adequate output of blood from one or both ventricles of the heart to meet the metabolic demands of the tissues. With a markedly weakened left ventricle or right ventricle or both, the volume of blood presented to the heart is in excess of the heart's capacity to move it along. Consequently, fluid builds up behind the heart. With a weakened left ventricle or right ventricle or both, there is a shift of large volumes of blood from the systemic circulation into the pulmonary (lung) circulation. If the inability to move the volume of blood forward is due to a left heart side problem without the right side falling as well, blood continues to be pumped into the lungs by the normal right heart side, while it is not pumped adequately out of the lungs by the left heart side. As the volume of blood in the lungs increases, the pulmonary vessels enlarge, pulmonary venous congestion develops, and, once the pulmonary capillary pressure rises above a critical point, fluid begins to filter out of the capillaries into the interstitial spaces and alveoli (air sacs in the lungs where exchange of oxygen and carbon dioxide occurs), resulting in pulmonary edema. Subsequently this can lead to pleural effusion (effusion is the escape of fluid into a part) and abdominal effusion. If the abnormality lies in the right heart side or the pulmonary arteries, limiting the ability to move blood forward, then congestion occurs behind the right heart side (causing pleural effusion and/or build up of fluid in the abdomen).

Although advances in pharmacology have led to better treatment, 50% of the patients with the most advanced stage of heart failure die within a year. Typically, heart failure patients receive several chronic oral therapies, including diuretics, ACE inhibitors, beta-blockers and inotropic agents.

A majority of patients are treated with drug therapy, but for patients with advanced CHF, device-based therapy or transplantation are their only alternatives. A large number of patients with advanced CHF have received left ventricular assist devices, and a number of promising technologies, including biventricular pacing and defibrillators and ventricular assist devices represent growing fields.

U.S. Pat. No. 6,763,267 relates to a ventricular conduction delay trending system and method for ascertaining the condition of the heart's conduction system in a patient treated for congestive heart failure with pacing therapy. Ventricular activation patterns are monitored over time in order to detect changes in the heart's conduction system that may occur due to physiological regeneration of conduction pathways. The activation patterns are reflected by electrogram signals detected from different ventricular locations during one heart cycle. By measuring the difference in conduction times of an excitation impulse travelling from the AV node to the different ventricular locations, a parameter representative of the hearts conduction system is obtained that may be used to adjust the pacing therapy in accordance therewith.

SUMMARY OF THE INVENTION

An object of the present invention is to provide an improved heart stimulating device for monitoring congestive heart failure.

The present invention is based upon the well-known fact that the heart rate variability decreases as CHF worsens. One reason to this may be decreased autonomic control and it has been found to correlate well with the degree of heart failure.

The invention is based on the inventors finding that patients suffering from CHF not only have a decreased heart rate variability, but also a decreased variability of the atrio-ventricular conduction time occurs, because it is controlled in the same way. The variability, in particular the standard deviation of the intrinsic atrio-ventricular conduction times was analyzed for nine CHF patients and found to be lower than in a control group of patients not suffering from CHF.

The above object is achieved in accordance with the present invention by a heart monitoring device for indicating congestive heart failure having a processor, and a sensor that senses at least two heart events during one heart cycle at different locations of the heart, and that supplies signals related to the sensed event to the processor. The processor determines at least one heart time interval between the sensed events in the same heart cycle, and determines a congestive heart failure indicator value that indicates the degree of congestive heart failure based on a variability measure calculated from at least two of the aforementioned heart time intervals from at least two different heart cycles. The indicator value is determined in relation to previously obtained or calculated indicator values.

According to a preferred embodiment of the present invention the intrinsic PR interval is regularly measured for a predetermined period of time in order to assess its variability. This is done typically once a day, preferably when the patient is at rest.

The variability measures—or a linear or non-linear combination of them—may be stored in the memory of the device to form a trend. This trend may later be displayed to the physician at the time of follow-up.

As mentioned above, the variability of the PR intervals is related to the neural control of the heart rhythm. Low heart rate variability (i.e. variability of the time between heart beats, e.g. consecutive heart beats) has been shown to correlate to the degree of illness and the same have been found with regard to PR interval variability.

If a patient has atrial asystole, i.e. the automaticity of the atria is extremely low and atrial pacing is present for nearly 100% of the time, the PR interval is impossible to measure as there are no P waves. In that case, or in other cases when atrial pacing is very important, the variability of the AR interval may be used instead of the PR interval.

The present invention may be used in implantable devices provided with one atrial electrode and at least one ventricular electrode, i.e. both dual-chamber and biventricular devices, the time from the P wave to the first or second electrode, or both of them, may be used to perform the variability calculations.

According to an alternative embodiment the present invention is instead implemented in a conventional ECG equipment provided with surface electrodes.

As used herein, the term "variability" denotes the degree of changes or variations of a predetermined entity from time to time.

The measures of variability of the PR intervals or other intervals may include the standard deviation, the range (i.e. max value-min value), SDNN (the mean of the standard deviation of e.g. 5 minute periods) etc. The invention is not limited to the use of just these measures.

BRIEF DESCRIPTION OF THE DRAWINGS

FIG. 1 shows a schematic block diagram illustrating a preferred embodiment of the present invention.

FIG. 2 shows a flow chart illustrating essential steps performed in accordance with a preferred embodiment of the present invention.

DESCRIPTION OF THE PREFERRED EMBODIMENTS

Figure 3:
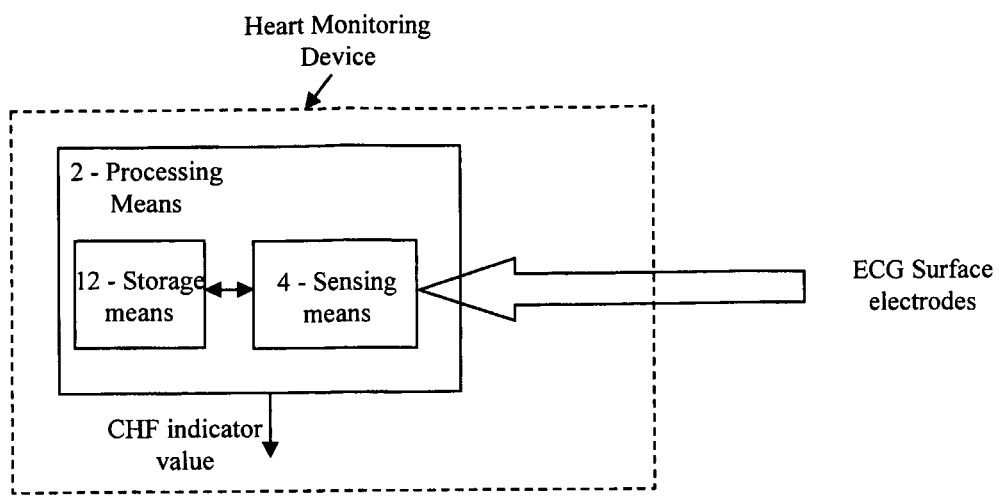
FIG. 3 shows a schematic block diagram illustrating an alternative embodiment of the present invention.

FIG. 1 shows a schematic block diagram illustrating a preferred embodiment of the present invention. FIG. 1 shows an implantable heart monitoring device for indicating congestive heart failure (CHF) having a processor 2 and a sensor 4 that senses at least two heart events via at least one electrode lead 8, 10. In the figure an atrial lead 8 is provided with an electrode for sensing electrical heart signals in the right atrium and a ventricular lead 10 is provided with an electrode for sensing electrical heart signals in the right ventricle.

According to another preferred embodiment the heart events are sensed in the right and left ventricles.

According to still another preferred embodiment the heart events are sensed in the left atrium and in the right or left ventricles. Those skilled in the art is familiar to electrode leads specifically adapted for pacing and sensing in the left side of the heart, in particular via coronary sinus and the great veins of the heart. Therefore these types of leads will not be further described herein.

In most cases the heart event sensed in the right or left atrium is an intrinsic event but may also be a stimulated heart event.

The heart monitoring device may be any implantable heart stimulating device, e.g. a pacemaker, a cardioverter or a defibrillator.

The heart events are sensed, during one heart cycle, at different locations of the heart and signals related to the sensed events are applied to the processing means that determines at least one heart time interval between the sensed events in the same heart cycle. The processing means is then adapted to determine a congestive heart failure indicator value indicating the degree of CHF based upon a variability measure calculated from at least two heart time intervals from at least two heart cycles. The indicator value is determined in relation to previous indicator values. Preferably, the variability measure is calculated from at least two heart time intervals from consecutive heart cycles.

The variability measure may be any suitable parameter indicating the variability of the measured intervals. Among those is in particular preferred the standard deviation of the heart time intervals, the difference between heart time intervals, and the mean of the standard deviation of the heart time intervals.

According to an alternative embodiment of the present invention the congestive heart failure indicator value is determined from a combination of at least two different variability measures.

The variability measure calculation is based upon sensed heart event signals preferably obtained during a predetermined time period of 4-8 minutes measured at a regular basis, e.g. once a day.

Furthermore, the processing means includes a storage unit 12 where the determined CHF indicator values are stored in order to be transmitted during a follow-up procedure to an external programming unit (not shown) for further analysis and display.

According to an alternative embodiment the sensed heart events are stored in the storage unit 12 in order to be transmitted during a follow-up procedure to an external programming unit (not shown) where the CHF indicator value indicating the degree of CHF is determined at a later time.

FIG. 2 shows a flow chart illustrating essential steps performed in accordance with a preferred embodiment of the present invention. At least two heart events are sensed during the same heart cycle by the sensing means, preferably in the right atrium (RA) and in the right ventricle (RV). The sensed events are then identified and a heart time interval between the sensed events is determined. A congestive heart failure indicator value indicating the degree of CHF based upon a variability measure is calculated from at least two heart time intervals from at least two heart cycles (i.e., at least from a first and from a second of the heart cycles). The indicator value is determined in relation to previous indicator values and is preferably stored in the storage means.

FIG. 3 shows a schematic block diagram illustrating an alternative embodiment of the present invention. In this embodiment the present invention is instead implemented in a conventional ECG equipment provided with extracorporeal surface electrodes. The signals sensed by the surface electrodes are applied to the sensing means provided with means for identifying the relevant heart events required to determine the heart time interval mentioned above in connection with the preferred embodiment described with reference to FIG. 1. The processing also takes place according to the above described preferred embodiment.

According to an alternative embodiment of the present invention also other time intervals may be used in order to establish the degree of CHF.

As most CHF patients receiving a biventricular pacing device have left bundle branch block (LBBB), there is a time interval from when the R wave reaches the right ventricular lead to when it reaches the left ventricular lead. This interval—called the RRRL interval—is also under autonomic control and may be used as the measured interval for the aforementioned device when determining a CHF indicator value. Measurement of the RRRL interval requires absence of pacing, which for some patients not is recommended, and this mode of operation may therefore be used only after careful considerations.

Although modifications and changes may be suggested by those skilled in the art, it is the intention of the inventor to embody within the patent warranted heron all changes and modifications as reasonably and properly come within the scope of his contribution to the art.

I claim as my invention:

1. A heart monitoring device for indicating congestive heart failure (CHF), comprising:

a processor;
a sensor configured to interact in vivo with a subject to sense IEGM (intracardiac electrogram) signals, in each of a plurality of different heart cycles, at least two heart events during one heart cycle at different locations of the heart, and to emit respective IEGM signals for each of said plurality of different heart cycles, representing said at least two heart events;
said processor being configured to obtain said IEGM signals as an input to said processor from said sensor;
said processor being configured to determine a heart time interval between said at least two heart events for a first of said plurality of different heart cycles and to calculate a first variability measure therefrom that measures a variation between said heart time interval in said first of said heart cycles and said heart time interval in at least another heart cycle, and to determine a first CHF indicator value, representing a degree of CHF of said subject, from said first variability measure;
said processor being configured to determine a heart time interval between said at least two heart events for a second of said plurality of different heart cycles and to calculate a second variability measure therefrom that measures a variation between said heart time interval in said second of said heart cycles and said heart time interval in at least another heart cycle, and to determine a second CHF indicator value, representing said degree of CHF of said subject, from said second variability measure and to determine a trend of said degree of CHF of said subject dependent on a relationship between said first CHF indicator value and said second CHF indicator value; and
each of said first variability measure and said second variability measure being selected from the group consisting of a standard deviation of, a mean of the standard deviation of, and a difference between, the respective heart time intervals; and
said processor being configured to generate a processor output signal, at an output of said processor, representing said trend.

2. A heart monitoring device as claimed in claim 1 comprising an electronic cardiac therapy delivery system configured to deliver an electronic cardiac therapy to the heart, and whenever said processor is configured to control operation of said electronic cardiac therapy delivery system with said output signal to adjust said electronic cardiac therapy dependent on said trend.

3. A heart monitoring device as claimed in claim 2 wherein said electronic cardiac therapy delivery system comprises a pulse generator selected from the group of pacing pulse generators, cardioverter pulse generators, and defibrillation pulse generators.

4. A heart monitoring device as claimed in claim 1 wherein said sensor comprises a first sensor configured to be placed in the right atrium of the heart to sense heart events in the right atrium, and a second sensor configured to be placed in the right ventricle to sense heart events in the right ventricle.

5. A heart monitoring device as claimed in claim 1 wherein said sensor comprises a first sensor configured to be placed in the right ventricle of the heart to sense heart events in the right ventricle, and a second sensor configured to be placed in the left ventricle to sense heart events in the left ventricle.

6. A heart monitoring device as claimed in claim 1 wherein said sensor comprises a first sensor configured to be placed in the left atrium of the heart to sense heart events in the left atrium, and a second sensor configured to be placed in the left ventricle to sense heart events in the left ventricle.

7. A heart monitoring device as claimed in claim 1 wherein said sensor comprises a first sensor configured to be placed in the left atrium of the heart to sense heart events in the left atrium, and a second sensor configured to be placed in the right ventricle to sense heart events in the right ventricle.

8. A heart monitoring device as claimed in claim 1 wherein said processor is configured to determine said CHF indicator value from a combination of at least two of said variability measures selected from the group consisting of a standard deviation of, a mean of the standard deviation of, and a difference between, the respective heart time intervals.

9. A heart monitoring device as claimed in claim 1 wherein said processor is configured to determine said variability measure from heart event signals sensed during a predetermined time period between four and eight minutes.

10. A heart monitoring device as claimed in claim 1 comprising a pacing pulse delivery system configured to deliver pacing stimulation pulses at least to the right atrium of the heart, and wherein said sensor comprises a sensor that senses stimulated heart events in the right atrium as one of said at least two heart events.

11. A heart monitoring device as claimed in claim 1 wherein said processor is configured to control operation of said sensor to sense said at least two heart events on a regular basis.

12. A heart monitoring device as claimed in claim 1 comprising a storage unit accessible by said processor, said processor being configured to store each determined CHF indicator value in said storage unit, and said storage unit being extracorporeally accessible for readout of the CHF indicator values stored therein.

13. A heart monitoring device as claimed in claim 1 wherein said sensor comprises extracorporeal surface electrodes that sense said at least two heart events during one heart cycle.

14. A heart monitoring device as claimed in claim 1 comprising a storage unit accessible by said processor, and wherein said sensor is configured to emit said sensor signals into said storage unit at a first point in time, and wherein said processor is configured to access said storage unit, at a second point in time after said first point in time, to retrieve said sensor signals therefrom and to determine said first and second variability measures and said first and second CHF indicator values.

* * * * *